(12) United States Patent
Kobayashi et al.

(10) Patent No.: US 10,904,429 B2
(45) Date of Patent: Jan. 26, 2021

(54) IMAGE SENSOR

(71) Applicant: SONY SEMICONDUCTOR SOLUTIONS CORPORATION, Atsugi (JP)

(72) Inventors: Masatsugu Kobayashi, Kanagawa (JP); Sayaka Shida, Kanagawa (JP); Koki Mitsunami, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 0 days.

(21) Appl. No.: 16/337,148

(22) PCT Filed: Oct. 19, 2017

(86) PCT No.: PCT/JP2017/037869
§ 371 (c)(1),
(2) Date: Mar. 27, 2019

(87) PCT Pub. No.: WO2018/105248
PCT Pub. Date: Jun. 14, 2018

(65) Prior Publication Data
US 2019/0289202 A1 Sep. 19, 2019

(30) Foreign Application Priority Data
Dec. 7, 2016 (JP) .................. 2016-237178

(51) Int. Cl.
*H04N 5/232* (2006.01)
*G02B 5/20* (2006.01)
(Continued)

(52) U.S. Cl.
CPC ......... *H04N 5/23229* (2013.01); *A61B 3/113* (2013.01); *G02B 5/20* (2013.01);
(Continued)

(58) Field of Classification Search
CPC ..... G06T 7/20–292; G06T 7/11; G06T 7/136; G06T 7/238; G06K 9/38; G06K 9/00335–00355; G06K 9/00597–00617
See application file for complete search history.

(56) References Cited

U.S. PATENT DOCUMENTS 9,830,708 B1 * 11/2017 Poliakov .............. G06K 9/38
2010/0201820 A1 8/2010 Lopota et al.
(Continued)

FOREIGN PATENT DOCUMENTS

JP 07-129781 A 5/1995
JP 2001-076156 A 3/2001
(Continued)

OTHER PUBLICATIONS

International Search Report and Written Opinion of PCT Application No. PCT/JP2017/037869, dated Jan. 23, 2018, 09 pages of ISRWO.

*Primary Examiner* — Paul M Berardesca
(74) *Attorney, Agent, or Firm* — Chip Law Group

(57) ABSTRACT

In an image sensor, high-speed recognition processing is performed using high-speed image data, which is different from low-speed image data used for displaying. In the image sensor, an imaging element captures an image of an object and generates frames of image data arranged in time series. A binarization processing unit performs binarization processing on each of the frames to generate binarized frames. A tracking processing unit generates a difference between binarized frames adjacent in time series and tracks a change in a position of the object included in the binarized frames.

17 Claims, 15 Drawing Sheets

(51) Int. Cl.
   *G06F 3/01*      (2006.01)
   *G06K 9/00*      (2006.01)
   *A61B 3/113*     (2006.01)
   *G06T 7/254*     (2017.01)
   *G06T 7/66*      (2017.01)
   *G06T 7/20*      (2017.01)

(52) U.S. Cl.
   CPC ........... *G06F 3/013* (2013.01); *G06K 9/0061* (2013.01); *G06T 7/20* (2013.01); *G06T 7/254* (2017.01); *G06T 7/66* (2017.01)

(56) References Cited

U.S. PATENT DOCUMENTS

| | | | |
|---|---|---|---|
| 2013/0215388 A1* | 8/2013 | Imamura | G06T 7/0012 351/206 |
| 2015/0325004 A1* | 11/2015 | Utsunomiya | A61B 5/742 382/103 |
| 2016/0140390 A1* | 5/2016 | Ghosh | G06K 9/00597 348/78 |
| 2018/0174309 A1* | 6/2018 | Hoshino | G06T 7/74 |
| 2019/0166345 A1* | 5/2019 | Katayama | H04N 5/232 |
| 2019/0206022 A1* | 7/2019 | Katayama | G06T 1/20 |

FOREIGN PATENT DOCUMENTS

| | | |
|---|---|---|
| JP | 2008-287594 A | 11/2008 |
| JP | 2008-2587594 A | 11/2008 |
| JP | 2012-238293 A | 12/2012 |
| JP | 2013-020311 A | 1/2013 |
| WO | 2010/084902 A1 | 7/2010 |

\* cited by examiner

IMAGE SENSOR

CROSS REFERENCE TO RELATED APPLICATIONS

This application is a U.S. National Phase of International Patent Application No. PCT/JP2017/037869 filed on Oct. 19, 2017, which claims priority benefit of Japanese Patent Application No. JP 2016-237178 filed in the Japan Patent Office on Dec. 7, 2016. Each of the above-referenced applications is hereby incorporated herein by reference in its entirety.

TECHNICAL FIELD

The present technology relates to an image sensor. More particularly, the present invention relates to an image sensor for carrying out a recognition process using captured image data.

BACKGROUND ART

Conventionally, various recognition processes are performed by using captured image data. As an example of such recognition processes, there has been proposed a terminal device incorporating a man-machine interface for recognizing gestures such as a human body movement and a hand movement as operation information from captured image data (see Patent Document 1, for example).

CITATION LIST

Patent Document

Patent Document 1: Japanese Patent Application Laid-Open No. 2013-020311

SUMMARY OF THE INVENTION

Problems to be Solved by the Invention

The above-described conventional technique is roughly divided into a data flow for outputting image data as a display image and a data flow for extracting necessary information from the image data and performing recognition processing. In order to display an image, processing speed of about 30 to 120 fps (frame/second) is sufficient in general but the processing speed is in sufficient to perform advanced recognition processing. That is, a low frame rate image captured by a normal camera is not suitable for measurement of a moving object, since its frame image interval is wide and real-time property is reduced in measurement using the image processing based on a movement such as a movement amount of an object, a movement speed, a rotation speed, and the like. Also, in order to detect an object that operates at high speed, processing such as frame interpolation or the like is needed; however, to analyze such an image, a large capacity database for storing images and a large amount of processing time are needed.

The present technology has been developed in view of such a situation and has an object to provide a processing unit necessary for recognition processing in an image sensor and to perform high-speed recognition processing using high-speed image data different from low-speed image data for display.

Solutions to Problems

The present technology has been made to solve the above problem and a first aspect of the present technology is an image sensor including an imaging element configured to capture an image of an object and generate frames of image data arranged in time series, a binarization processing unit configured to binarize each of the frames to generate binarized frames, and a tracking processing unit configured to generate a difference between the binarized frames adjacent in time series and track a change in a position of the object included in the binarized frames. With this configuration, there is an effect that the captured frame can be binarized in the image sensor and the object can be tracked.

Furthermore, in the first aspect, a filter processing unit configured to perform filter processing on each of the frames may further be included, and the binarization processing unit may perform the binarization processing on each of the frames on which the filter processing has been performed. With this configuration, there is an effect that filtering processing can be performed on each of the frames.

Furthermore, in the first aspect, a moment generation unit configured to calculate a moment of the object included in the binarized frames on the basis of a result of the tracking processing unit may further be included. With this configuration, there is an effect that the amount of the change in the area of the object included in the binarized frame can be generated.

Furthermore, in the first aspect, a barycentric position generation unit configured to generate a barycentric position of the object included in the binarized frames on the basis of the moment generated by the moment generation unit may further be included. With this configuration, there is an effect that the barycentric position of the object included in the binarized frames can be generated.

Furthermore, in the first aspect, an aggregation processing unit configured to perform aggregation processing on the object on the basis of the barycentric position of the object generated by the barycentric position generation unit may further be included. With this configuration, there is an effect that aggregating processing can be performed on the object.

Furthermore, in the first aspect, a display control unit configured to display a result of the aggregation processing by the aggregation processing unit may further be included. With this configuration, there is an effect that the result of the aggregation processing can be displayed.

Furthermore, in the first aspect, the aggregation processing unit may aggregate at least one of a number of the objects, its size, and its movement rate. With this configuration, there is an effect that the number of objects, the size, and the movement rate can be aggregated.

Furthermore, in the first aspect, the aggregation processing unit may detect a change in a shape of the object, and the tracking processing unit may start tracking in a case where the change in the shape of the object is detected. With this configuration, there is an effect that the object can be tracked in response to the detection of the change in the shape of the object.

Furthermore, in the first aspect, the aggregation processing unit may measure the speed of the object and calculate a statistical value of the speed of the object in a case where there are a plurality of objects. With this configuration, there is an effect that statistical values of the speed of the plurality of objects are calculated.

Furthermore, in the first aspect, the imaging element may capture an image of an eye of a living body as the object, the binarization processing unit may detect a pupil in the captured image of the eye of the living body, the tracking processing unit may tracks a line-of-sight in the captured image of the eye of the living body, the moment generation unit may calculate an area of the pupil in the captured image of the eye of the living body, and the aggregation processing unit may detect blinking on the basis of the area of the pupil and time that the pupil is continuously recognized. With this configuration, there is an effect that the blinking can be detected from the captured image of the eye. Furthermore, in this case, an interface for accepting an operation input according to a manner of blinking may further be included. With this configuration, there is an effect that an operation may be input according to the manner of the blinking.

Furthermore, in the first aspect, the barycentric position generation unit may generate a barycentric position of the pupil in the captured image of the eye of the living body, and the aggregation processing unit may determine the line-of-sight direction from the barycentric position of the pupil. With this configuration, there is an effect that the line-of-sight direction can be determined on the basis of the captured image of the eye. Furthermore, in this case, an interface configured to accept an operation input according to the manner of the blink and the line-of-sight direction may further be included. With this configuration, there is an effect that an operation can be input according to the manner of the blinking and the line-of-sight direction.

Furthermore, in the first aspect, the aggregation processing unit may control the binarization processing unit to perform the detection of the pupil again when the blinking is detected. With this configuration, there is an effect that the detection of the pupil is restarted in response to detection of the blinking.

Furthermore, in the first aspect, the aggregation processing unit may measure the speed of the object and detect an abnormality in a case where the speed of the object does not satisfy a predetermined condition. With this configuration, there is an effect that the abnormality is detected by the speed in the captured image of the object.

Furthermore, in the first aspect, the aggregation processing unit may measure a vibration amount of the object and detect an abnormality in a case where the vibration amount of the object does not satisfy a predetermined condition. With this configuration, there is an effect that the abnormality is detected by the vibration amount in the captured image of the object.

Furthermore, in the first aspect, the aggregation processing unit may measure the rotation amount of the object and detect an abnormality in a case where the rotation amount of the object does not satisfy a predetermined condition. With this configuration, there is an effect that an abnormality is detected by the rotation amount in the captured image of the object.

Effects of the Invention

According to the present technology, it is possible to achieve an excellent effect that high-speed recognition processing can be performed in the image sensor. Note that effects described here should not be limited and there may be any effect described in the present disclosure.

MODE FOR CARRYING OUT THE INVENTION

In the following, a mode for implementing the present technology (hereinafter, referred to as an embodiment) will be described. The description will be given in the following order.

1. Embodiment (Configuration example of image processing system)
2. First application example (Example of cell measurement)
3. Second application example (Example of cell division measurement)
4. Third application example (Example of cell motion measurement)

5. Fourth application example (Examples of blink detection and line-of-sight detection)

6. Fifth application example (Example of blood flow velocity measurement)

7. Sixth application example (Example of malfunction detection by vibration amount measurement)

8. Seventh application example (Example of malfunction detection by rotation amount measurement)

1. Embodiment

Figure 1:
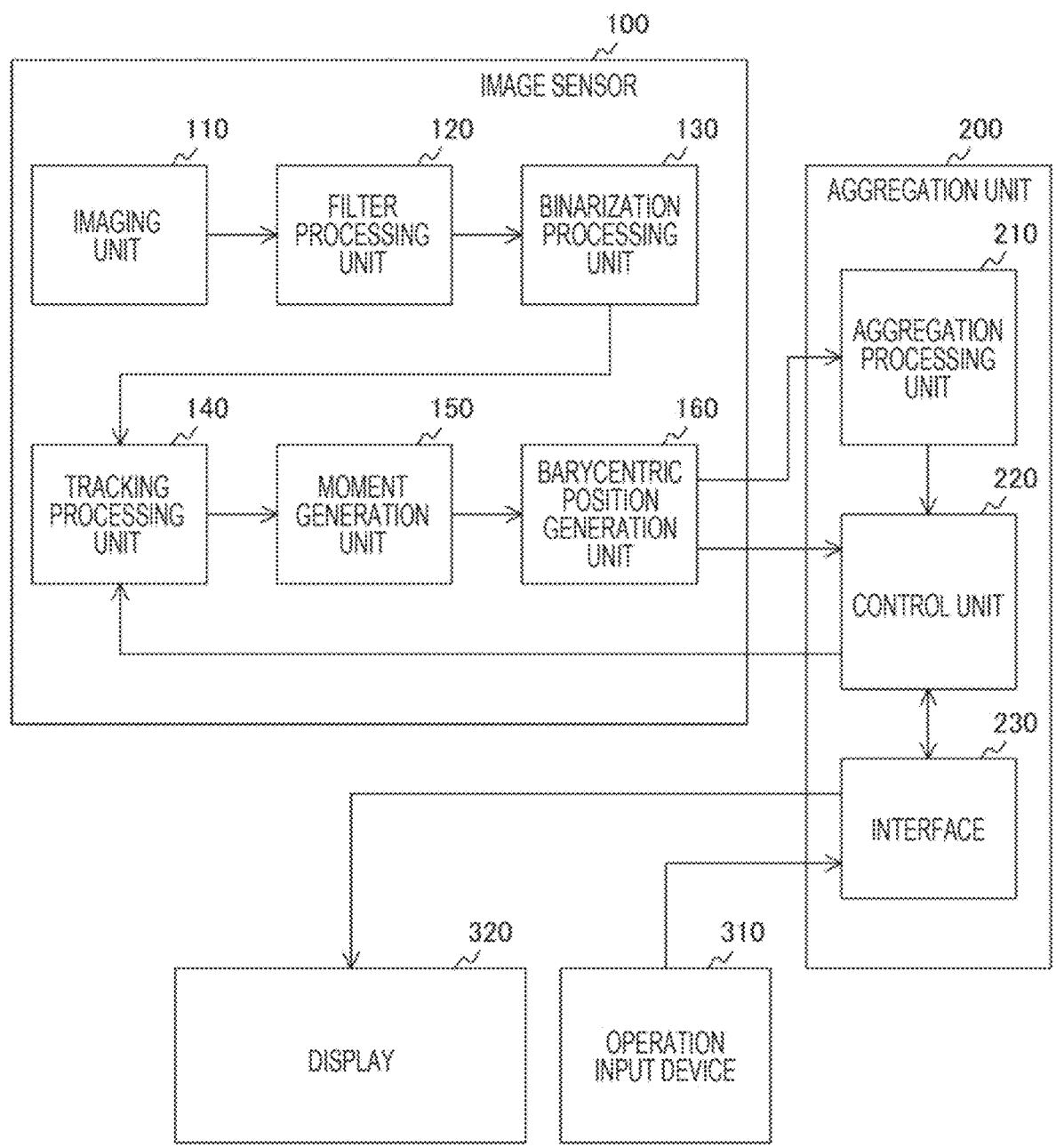
FIG. 1 is a diagram illustrating a configuration example of an image processing system according to an embodiment of the present technology.

FIG. 1 is a diagram illustrating a configuration example of an image processing system according to an embodiment of the present technology. The image processing system according to the present embodiment includes an image sensor 100, an aggregation unit 200, an operation input device 310, and a display 320.

The image sensor 100 captures an image of a subject including a target object and performs recognition processing of the target object. The aggregation unit 200 performs aggregation on the basis of various pieces of data obtained by the image sensor 100. The operation input device 310 receives an operation input from outside. The display 320 displays an aggregation result obtained by the aggregation unit 200.

Note that, here, as an example, a mode in which each function of the aggregation unit 200 is independent from the image sensor 100 will be described; however, there may be a mode in which a part or all of the functions of the aggregation unit 200 are incorporated in the image sensor 100.

The image sensor 100 includes an imaging unit 110, a filter processing unit 120, a binarization processing unit 130, a tracking processing unit 140, a moment generation unit 150, and a barycentric position generation unit 160.

The imaging unit 110 is an imaging element that captures an image of a subject including a target object. The imaging unit 110 generates frames of image data arranged in time series at a predetermined frame rate. Here, as the frame rate, a high frame rate of 1000 frames (1000 fps) or more per second is assumed. It is not needed to supply all frames of the image data captured by the imaging unit 110 to the outside of the image sensor 100. Image data at a high frame rate is for later described recognition processing and, for displaying purpose, a lower frame rate is sufficient. In other words, by keeping the image data of the high frame rate as reference in the image sensor 100, a bandwidth of the image sensor 100 can be effectively used. Note that the imaging unit 110 is an example of an imaging element described in the claims. Also, the target object may be an object widely including non-living things in addition to a living thing such as a person or an animal.

The filter processing unit 120 performs filter processing on each frame of the image data captured by the imaging unit 110. As the filter processing in the filter processing unit 120, for example, there may be noise removal processing using a moving average filter a median filter or the like, outline detection processing using a Sobel filter or the like, edge detection using a Laplacian filter or the like, and the like. Furthermore, a number of target objects included in the image can also be calculated by obtaining an Euler number of the image by the filter processing unit 120. The Euler number is a number in which a number of openings is subtracted from a number of components.

The binarization processing unit 130 performs binarization processing on each of the frames on which the filter processing is performed by the filter processing unit 120. The binarization processing unit 130 binarizes the image data on the basis of histogram information of luminance and colors included in the image data of each frame and generates a binarized frame including binarized data.

Regarding the binarized frame generated by the binarization processing unit 130, the tracking processing unit 140 generates a difference between frames being adjacent in time series to detect a target object included in the binarized frame and track a change in a position of the target object. In a case where a target object is detected, a specific region in the image can be designated as a measurement target.

The moment generation unit 150 calculates a moment of a two-variable function in the binarized frame on the basis of a result by the tracking processing unit 140. A zero-order moment represents a change amount of the area of the target object included in the binarized frame and is a value that is invariant to rotation or scaling of the image.

The barycentric position generation unit 160 generates a barycentric position of the target object included in the binarized frame on the basis of the moment generated by the moment generation unit 150. A value obtained by dividing each primary moment in a horizontal direction and a vertical direction by the zero-order moment respectively represents the barycentric position.

The aggregation unit 200 includes an aggregation processing unit 210, a control unit 220, and an interface 230. The aggregation processing unit 210 performs aggregation processing on the basis of various data obtained by the image sensor 100. As explained in later described application examples, the aggregation processing unit 210 performs necessary processing according to an application to be operated. The control unit 220 controls operation of the aggregation unit 200 and each unit of the image sensor 100. The interface 230 controls an interface with outside. In this example, the interface 230 is connected to the display 320 and performs an input/output control for causing the display 320 to display the aggregation result obtained by the aggregation unit 200. Note that the interface 230 is an example of an interface and a display control unit described in the claims.

Although a route through which the output from the barycentric position generation unit 160 is supplied to the aggregation processing unit 210 and the control unit 220 is indicated clearly in this figure, a route to provide various data from each unit of the image sensor 100 to the aggregation unit 200 may be provided according to need.

Such a configuration allows a program calculation to be embedded in the processing on a frame basis according to the recognition processing, and a calculation result for each frame such as a movement amount and a size of the target object, a movement direction, or histogram information can be output as sensing information at high speed. Furthermore, without processing the image in a later stage, analysis can be performed by using the calculation result only.

2. First Application Example

Figure 2:
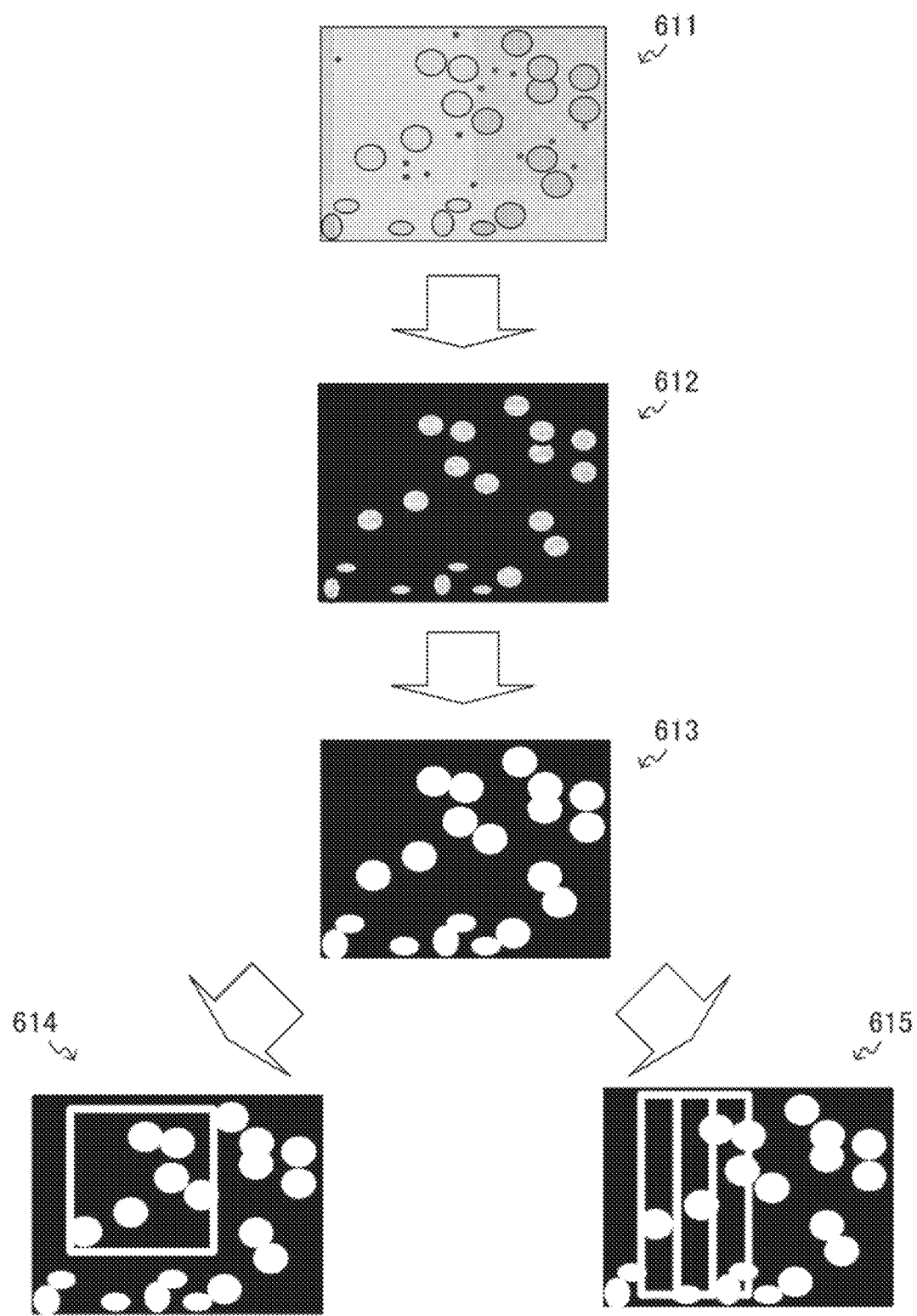
FIG. 2 is a diagram illustrating an example of cell measurement in a first application example according to the embodiment of the present technology.

FIG. 2 is a diagram illustrating an example of cell measurement in a first application example according to the embodiment of the present technology. In order to perform cell measurement using the image processing system according to the present embodiment, a cell culture plate or the like for culturing cells to be measured is prepared, and an image is captured by the imaging unit 110 via a microscope. With this configuration, as illustrated with an image 611, motion of a cell can be observed as a moving image including time-series frames at a high frame rate.

In each of the captured frames, noise which is not in a constant size is removed by the filter processing unit 120. In addition, in the filter processing unit 120, as illustrated in an image 612, outline detection processing by a Sobel filter or the like is performed.

After the outline detection processing is performed in the filter processing unit 120, the inside of the outline is validated in the binarization processing unit 130 and binarized as illustrated in an image 613. The white parts represent individual cells.

On the basis of the binarized image 613, the movement of each cell is tracked by generating a difference between frames in the tracking processing unit 140. Furthermore, the moment is calculated in the moment generation unit 150.

In a case where a specific region is defined as a measurement target by the operation input device 310 as illustrated in an image 614, an interframe difference and moment in the specific region are calculated and the movement rate of the cell in the specific region is calculated. Furthermore, in a case where a plurality of regions are defined as measurement targets by the operation input device 310 as illustrated in an image 615, a movement rate of the cell in each of the plurality of regions is calculated.

Figure 3:
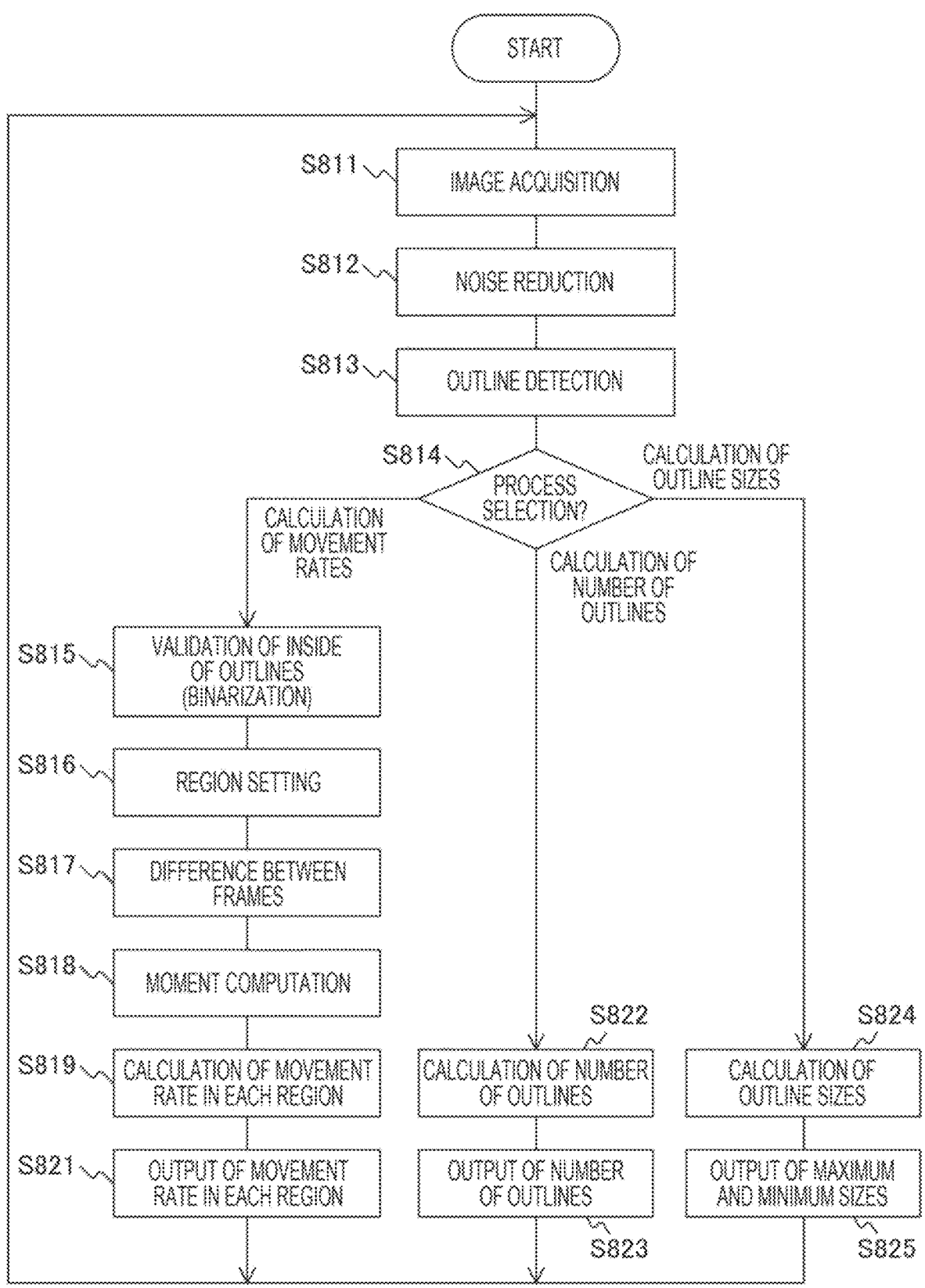
FIG. 3 is a flowchart illustrating an example of a processing procedure of the cell measurement in the first application example according to the embodiment of the present technology.

FIG. 3 is a flowchart illustrating an example of a processing procedure of cell measurement in the first application example according to the embodiment of the present technology.

First, image data including a cell to be measured is acquired (step S811). Therefore, an image of a cell culture plate is captured by the imaging unit 110 through, for example, a microscope. The acquired image data constitutes a time-series frame.

In each of acquired frames, noise which is not in a constant size is removed (noise reduction) by the filter processing unit 120 (step S812). Then, in the frames from which the noise has been removed, outline detection processing is performed in the filter processing unit 120 (step S813).

Thereafter, the process is selected according to an instruction from the operation input device 310 (step S814). In a case where calculation of the movement rate of the cell is selected, inside of the outline of the frame to which the outline detection processing is performed is validated in the binarization processing unit 130, and the frame is binarized (step S815).

In a case where a specific region is set as a measurement target according to an instruction from the operation input device 310 (step S816), the difference between the frames adjacent in time series in this specific region is generated by the tracking processing unit 140 (step S817). Then, the moment computation is performed by the moment generation unit 150 on the set specific region (step S818).

On the basis of the computed moment, the aggregation processing unit 210 calculates the movement rate of the cell in each specific region (step S819). The calculated movement rate of the cell is displayed on the display 320 via the interface 230 (step S821).

In a case where the calculation of a number of outlines is selected (step S814), the aggregation processing unit 210 obtains the Euler number of the image on which the outline detection processing has been performed in the binarization processing unit 130 to calculate a number of the target objects included in the image (step S822). For example, a desired cell size is preset in units of nanometers, and a number of cells in the predetermined size is calculated. The number of outlines calculated in this manner is displayed on the display 320 via the interface 230 (step S823).

In a case where calculation of an outline size is selected (step S814), the aggregation processing unit 210 calculates a size of an outline included in the image on the basis of the moment generated by the moment generation unit 150 (step S824). Thus, the size of each of a plurality of cells included in the image can be obtained. The aggregation processing unit 210 sorts obtained cell sizes and obtains a maximum value and a minimum value of the cell sizes. The maximum and minimum values of the cell sizes are displayed on the display 320 via the interface 230 (step S825).

These processes are repeatedly performed on each of the frames of image data arranged in time series.

Note that, in this example, since it is assumed that the aggregation processing unit 210 operates independently, the processing of steps S815 to S818 and the processing of steps S822 to S825 can be executed in parallel with each other.

3. Second Application Example

Figure 4:
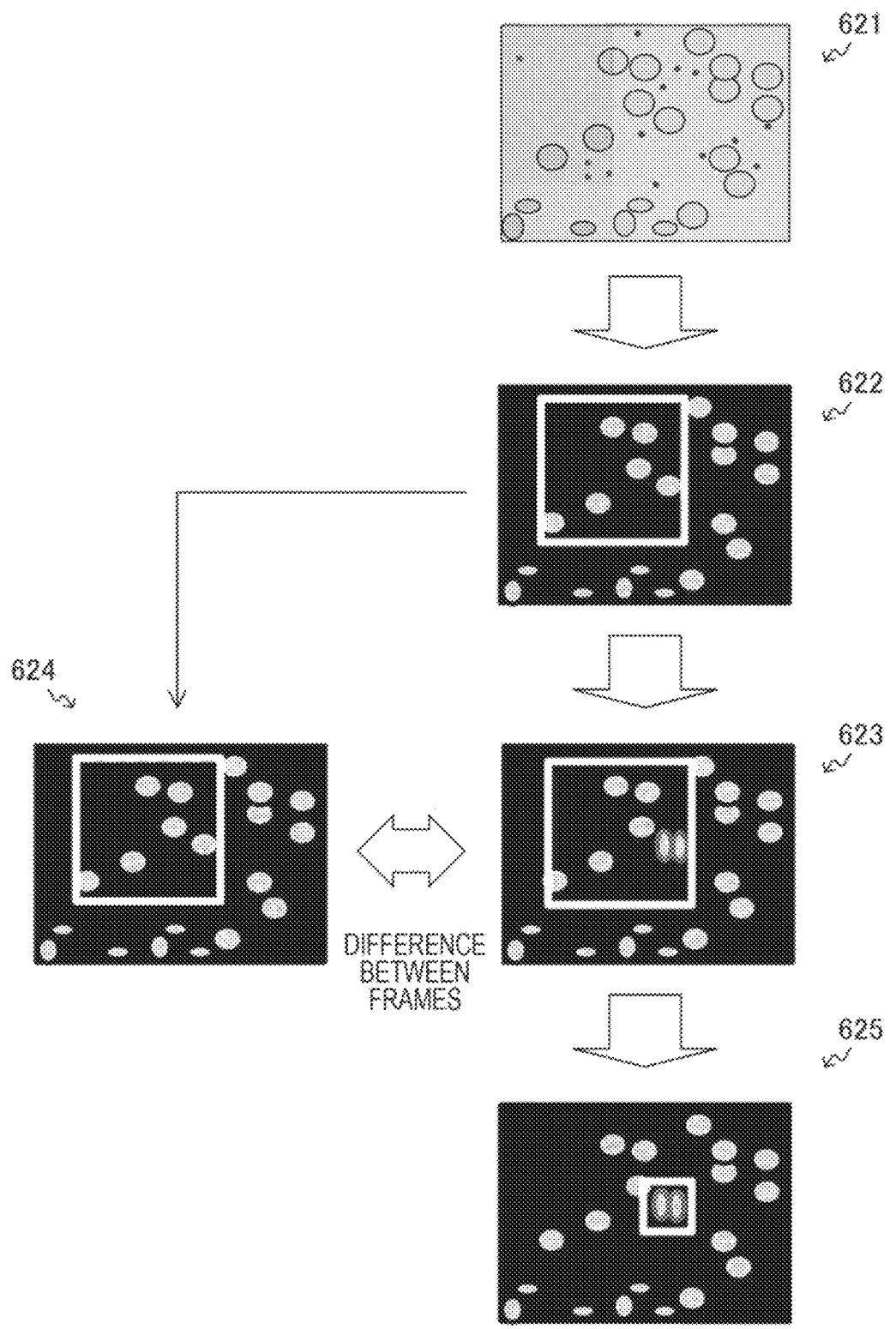
FIG. 4 is a diagram illustrating an example of cell division measurement in a second application example according to the embodiment of the present technology.

FIG. 4 is a diagram illustrating an example of cell division measurement in a second application example of the embodiment according to the present technology. In order to perform cell division measurement using the image processing system according to the present embodiment, a cell culture plate or the like for culturing cells to be measured is prepared in a similar manner as in the cell measurement example described above, and an image is captured by the imaging unit 110 via the microscope. As a result, as illustrated in an image 621, a cell movement can be observed as a moving image including time-series frames at a high frame rate.

In a similar as in the example of the above-described cell measurement, in each captured frame, noise which is not in a constant size is removed by the filter processing unit 120. In addition, in the filter processing unit 120, as illustrated in an image 612, outline detection processing by a Sobel filter or the like is performed. An image 622 obtained in this manner is maintained as an image 624 which illustrates a state immediately before cell division.

In a case where the operation input device 310 defines a specific region as a measurement target as illustrated in the image 622, a change in the number of outlines is detected in this specific region. In a case where the number of outlines changes as illustrated in an image 623, it is presumed that cell division occurred in the specific region. At the timing when this cell division occurs, a difference between the frames is generated, and from the result, the target is specified as illustrated in an image 625 and tracking is started. As a result, a subsequent action of the cell is observed.

Figure 5:
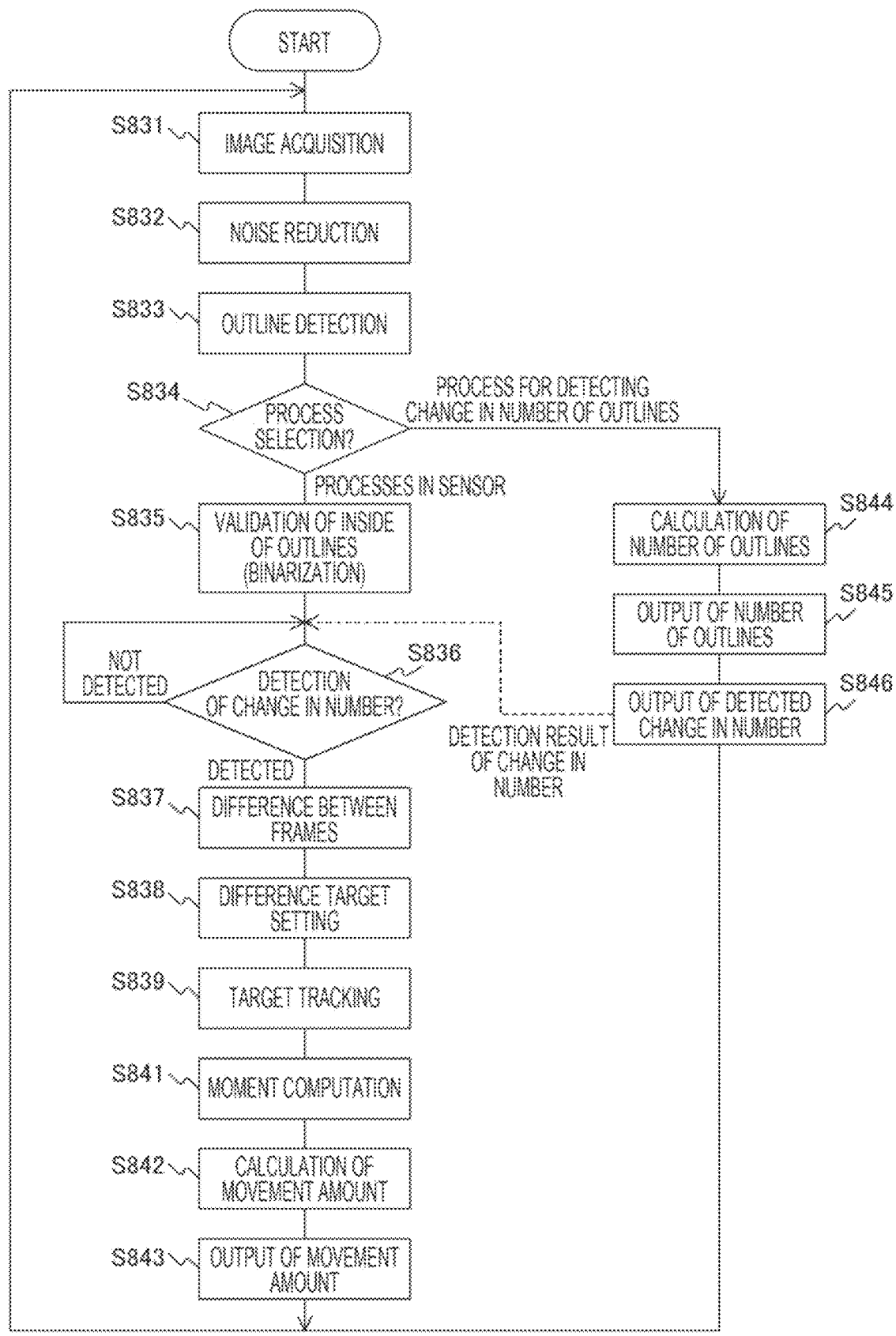
FIG. 5 is a flowchart illustrating an example of a processing procedure of the cell division measurement in the second application example according to the embodiment of the present technology.

FIG. 5 is a flowchart illustrating an example of a processing procedure of cell division measurement in the second application example of the embodiment according to the present technology.

First, image data including the cells to be measured is acquired (step S831). Therefore, an image of a cell culture plate is captured by the imaging unit 110 through, for example, a microscope. The acquired image data constitutes a time-series frame.

In each acquired frame, noise which is not in the constant size is removed by the filter processing unit 120 (step S832). Then, in the frame from which the noise has been removed, outline detection processing is performed in the filter processing unit 120 (step S833).

Thereafter, a process is selected according to an instruction from the operation input device 310 (step S834). In a case where the interlocking processing by the hardware in the image sensor 100 is selected, the inside of the outline of the frame in which the outline detection processing is performed is validated in the binarization processing unit 130, and the frame is binarized (step S835). Thereafter, the process stands ready until a change in the number of outlines is detected (step S836).

On the other hand, when the detection of the change in the number of outlines in the aggregation unit 200 is selected (step S834), the aggregation processing unit 210 calculates the Euler number of the image to which the outline detection processing is performed in the binarization processing unit 130 and calculates the number of outlines (step S844). The calculated number of outlines is displayed on the display 320 via the interface 230 (step S845). Then, in a case where a change in the number of outlines is detected, the control unit 220 notifies the tracking processing unit 140 of the detection (step S846).

In a case where detection of the change in the number of outlines is given in notification (step S836), the tracking processing unit 140 generates a difference between frames adjacent in time series (step S837). From this result, a target to be tracked is set (step S838), and target tracking by the tracking processing unit 140 is started (step S839). Then, with respect to the set target, a moment computation is performed by the moment generation unit 150 (step S841).

Then, the individual movement amount for each frame is calculated by the barycentric position generation unit 160 (step S842). In addition, the individual movement amount for each frame is aggregated in the aggregation processing unit 210, and the aggregated movement amount such as average speed or variation in speed is obtained as the result of aggregating the plurality of frames. Then, the individual movement amount and the aggregated movement amount obtained in this manner are displayed on the display 320 via the interface 230 (step S843).

These processes are repeatedly performed on each of the frames of image data arranged in time series.

Note that, in this example, since it is assumed that the aggregation processing unit 210 operates independently, the processing of steps S835 to S841 and the processing of steps S844 to S846 can be executed in parallel with each other.

4. Third Application Example

Figure 6:
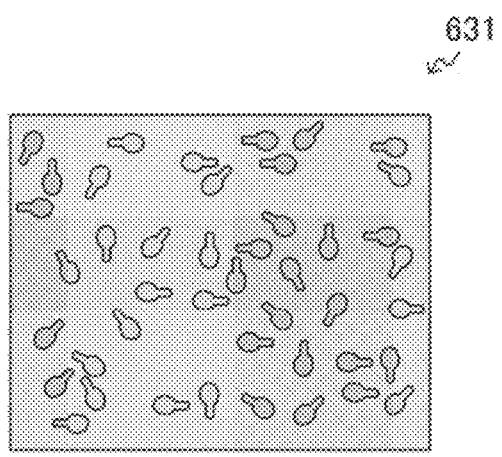
FIG. 6 is a diagram illustrating an example of cell motion measurement in a third application example according to the embodiment of the present technology.
Figure 6:
Figure 6:
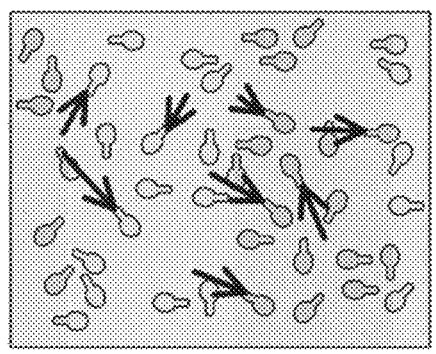

FIG. 6 is a diagram illustrating an example of cell motion measurement in a third application example of the embodiment according to the present technology. In order to perform cell motion measurement using the image processing system according to the present embodiment, a cell culture plate or the like for culturing cells as a measurement object is prepared in a similar manner as in the case of cell measurement described above, and an image is captured by the imaging unit 110 through a microscope. As a result, as shown in an image 631, cell movement can be observed as a moving image including time-series frames at a high frame rate.

In a similar as in the example of the above-described cell measurement, in each captured frame, noise which is not in a constant size is removed by the filter processing unit 120. Furthermore, binarization processing is performed in the binarization processing unit 130.

In a case where a specific region is defined as a measurement target by the operation input device 310, interframe difference and moment computation are performed in this specific region, and as illustrated in an image 632, movement amount of the cell in the specific region is calculated. In addition, a floating rate or a moving speed of the cell can be calculated.

Furthermore, the movement of a specific target is detected and a start of data analysis can be defined using the detection as a trigger. As a result, load of unnecessary image analysis can be reduced.

In addition, in a case where cells to be measured are individually defined, the movement speed of the cells can be calculated by performing target tracking in the tracking processing unit 140. Thus, for example, the degree of malignancy of a cancer cell or the like can be determined.

In addition, as a premise of high-speed imaging as described in the present embodiment, a migration rate that indicates a rate of active movements within a specific region can be measured even in a case of a target such as a sperm which needs a speed of about 150 fps and moves in an irregular manner.

Figure 7:
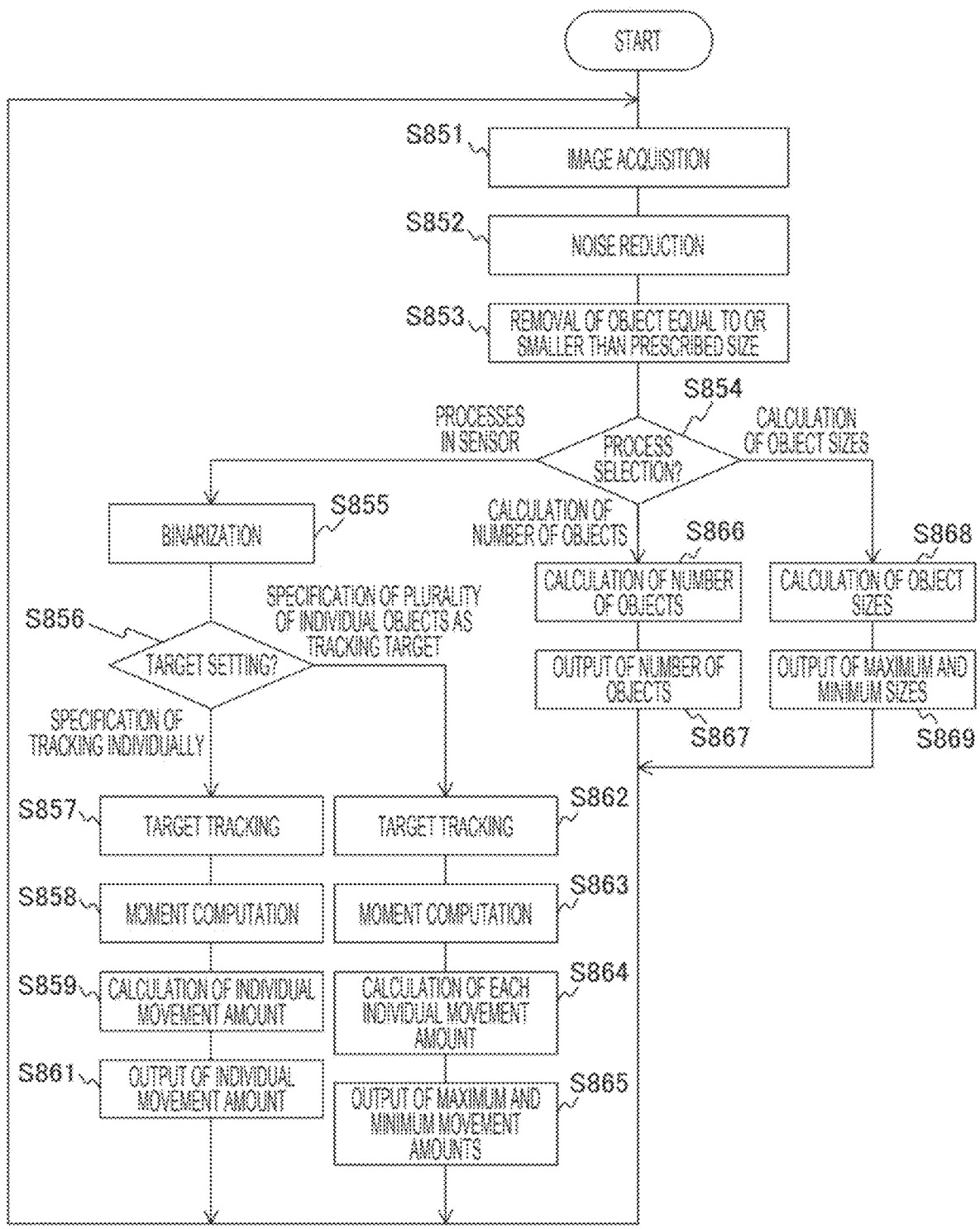
FIG. 7 is a flowchart illustrating an example of a processing procedure of the cell motion measurement in the third application example according to the embodiment of the present technology.

FIG. 7 is a flowchart illustrating an example of a processing procedure of cell motion measurement in the third application example of the embodiment according to the present technology.

First, image data including cells to be measured is acquired (step S851). Therefore, an image of a cell culture plate is captured by the imaging unit 110 through, for example, a microscope. The acquired image data constitutes a time-series frame.

In each acquired frame, noise which is not in the constant size is removed by the filter processing unit 120 (step S852). Then, in the frame from which the noise has been removed, the filter processing unit 120 removes a target object whose size is equal to or smaller than a prescribed size (step S853).

Thereafter, a process is selected according to an instruction from the operation input device 310 (step S854). In a case where interlock processing by the hardware in the image sensor 100 is selected, the binarization processing unit 130 performs binarization processing of the frame (step S855).

In a case where a single individual is set as a measurement target according to an instruction from the operation input device 310 (step S856), a difference between the frames adjacent in time series in the single individual is generated by the tracking processing unit 140 (step S857). Then, for that single individual, the moment computation is performed by the moment generation unit 150 (step S858). In addition, for each single individual, the individual movement amount (movement speed) is calculated by the barycentric position generation unit 160 (step S859). The individual movement amount obtained in this manner is displayed on the display 320 via the interface 230 (step S861).

In a case where a plurality of individuals are set as measurement targets according to an instruction from the operation input device 310 (step S856), a difference between frames adjacent in time series is generated by the tracking processing unit 140 for each of the plurality of individuals (step S862). Then, for the plurality of individuals, moment computation is performed by the moment generation unit 150 (step S863). Thereafter, for each of the plurality of individuals, an individual movement amount is calculated by the barycentric position generation unit 160 (step S864). The aggregation processing unit 210 sorts the obtained individual movement amounts and obtains a maximum value and a minimum value of the individual movement amounts. The maximum value and the minimum value of these individual movement amounts are displayed on the display 320 via the interface 230 (step S865).

In a case where calculation of the number of objects is selected (step S854), the aggregation processing unit 210 obtains the Euler number of the image and calculates the number of target objects included in the image (step S866). For example, a desired cell size is preset in units of nanometers, and a number of cells in the predetermined size is calculated. The number calculated in this manner is displayed on the display 320 via the interface 230 (step S867).

In a case where calculation of the size of the target object is selected (step S854), the aggregation processing unit 210 calculates the size of the target object included in the image on the basis of the moment generated by the moment generation unit 150 (step S868). With this configuration, the size of each of the plurality of target objects included in the image can be obtained. The aggregation processing unit 210 sorts the obtained sizes of the target objects and obtains a maximum value and a minimum value of the sizes of the target objects. The maximum value and the minimum value of the sizes of these target objects are displayed on the display 320 via the interface 230 (step S869).

These processes are repeatedly performed on each of the frames of image data arranged in time series.

Here, in this example, since it is assumed that the aggregation processing unit 210 operates independently, the processing of steps S855 to S858 and the processing of steps S866 to S869 can be executed in parallel with each other.

5. Fourth Application Example

Figure 8:
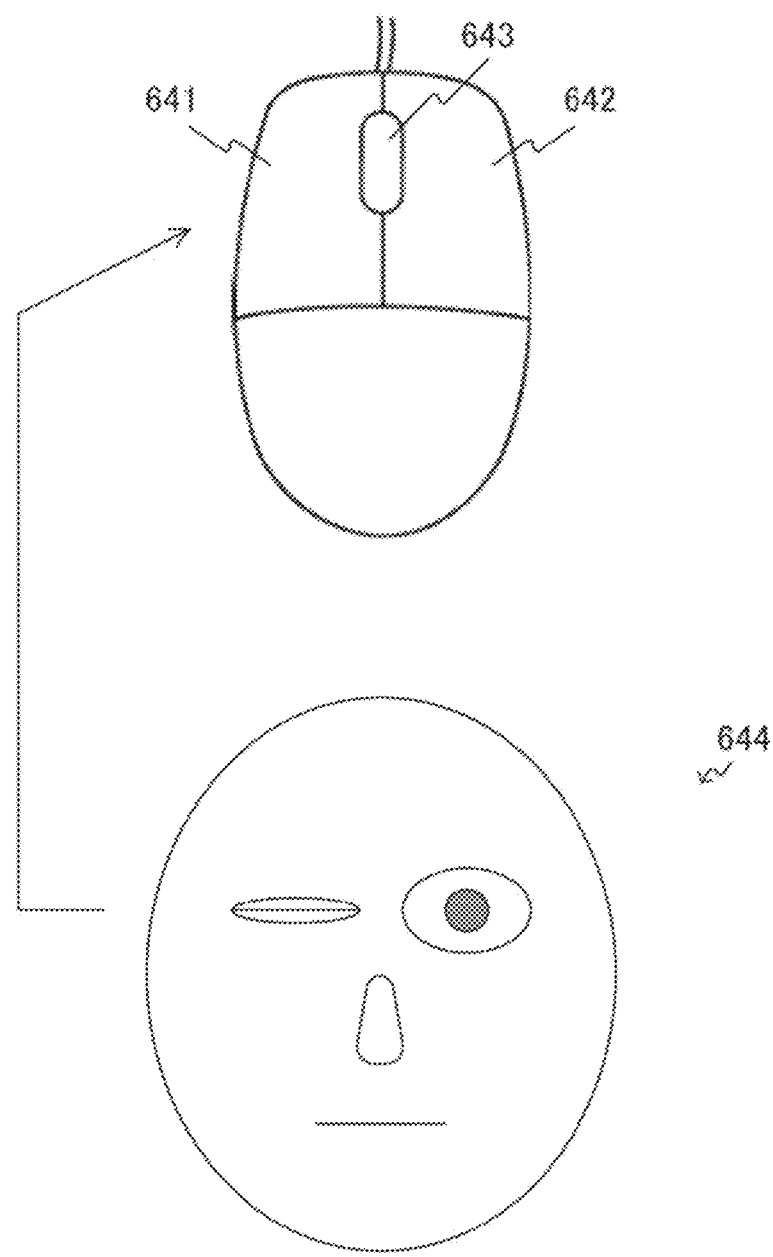
FIG. 8 is a diagram illustrating an example of blink detection and line-of-sight detection in a fourth application example according to the embodiment of the present technology.

FIG. 8 is a diagram illustrating an example of blink detection and line-of-sight detection in a fourth application example of the embodiment according to the present technology. In order to capture a blinking motion of a human being, a speed of 60 to 125 fps is required; however, by using the image processing system according to the present embodiment, an image of a human eye can be captured as a target object and it can be determined whether or not there is a blink by generating an area of a pupil and a duration time. Furthermore, by generating barycentric position of the pupils of both eyes, a line-of-sight direction can be determined.

This realizes a user interface that is not restricted by a use environment, and operation similar to that of a familiar device can be performed. In addition, since the left and right hands can be used freely, an advantage of the wearable device can be effectively utilized without being bound by the device.

For example, in a case where an image 644 including human eyes is captured and a wink of the left eye is detected, it is conceivable that an operation similar to an operation executed after pressing the left button 641 of the mouse will be performed. Furthermore, in a case where a wink of the right eye is detected, it is conceivable that an operation similar to an operation after the right button 642 of the mouse is pressed will be performed. Furthermore, according to the line-of-sight direction, it is conceivable that an operation similar to an operation executed in a case where the mouse wheel 643 is operated will be performed.

Figure 9:
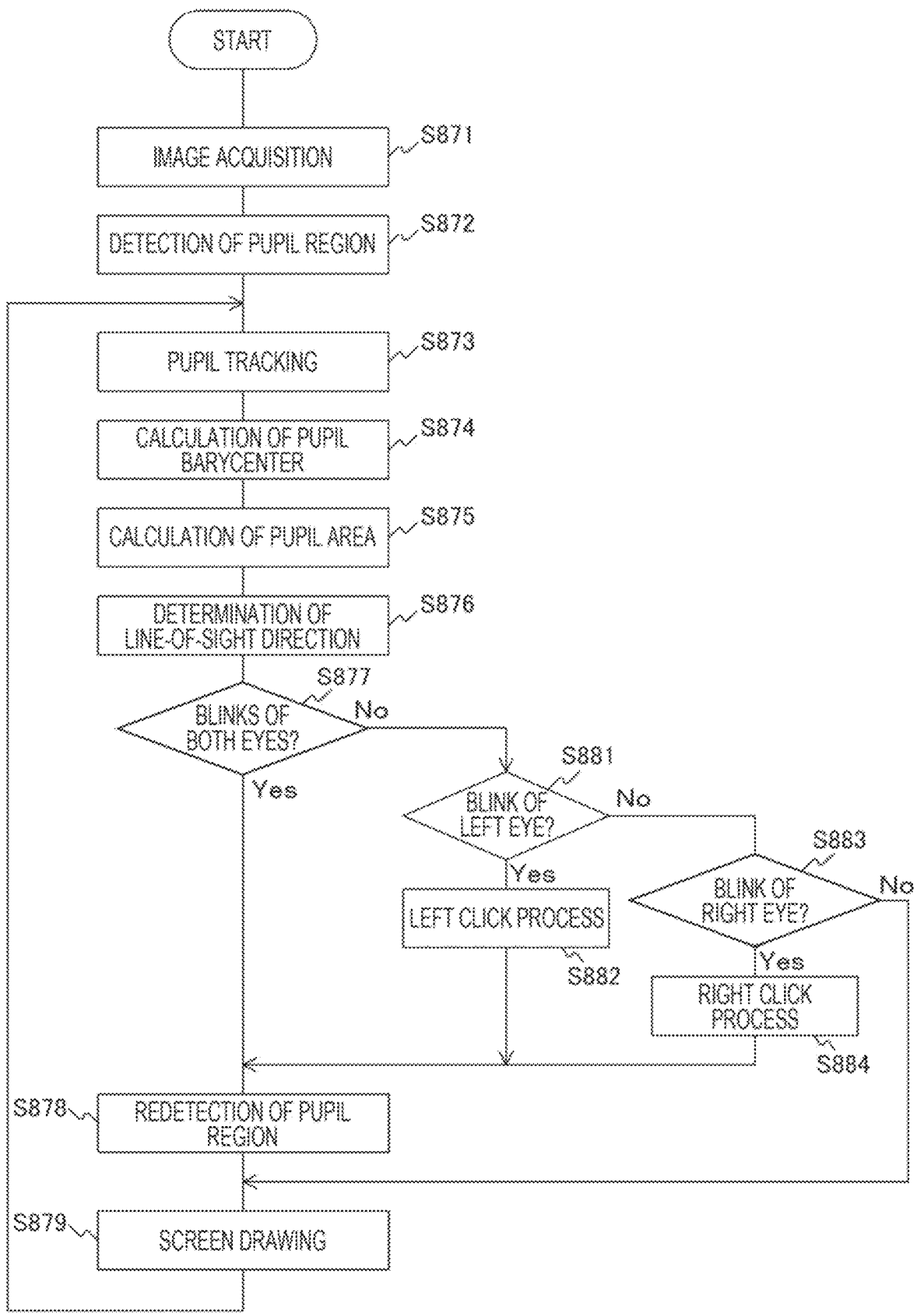
FIG. 9 is a flowchart illustrating an example of a processing procedure of the blink detection and line-of-sight detection in the fourth application example according to the embodiment of the present technology.

FIG. 9 is a flowchart illustrating an example of a processing procedure of blink detection and line-of-sight detection in a fourth application example of the embodiment according to the present technology.

First, image data including human eyes to be measured is acquired (step S871). For this configuration, for example, a wearable device or an eyewear device can be used as the imaging unit 110.

Then, binarization processing is performed in the binarization processing unit 130, and a pupil region is detected (step S872). Furthermore, in the tracking processing unit 140, the movement of the pupil is tracked (step S873).

With respect to the pupil recognized in this manner, the barycentric position of the pupil is calculated by the barycentric position generation unit 160 (step S874), the moment computation is performed by the moment generation unit 150, and the area of the pupil is calculated (step S875). As a result, a blink is detected. Also, on the basis of the barycenter of the pupil generated by the barycentric position generation unit 160, the line-of-sight direction is determined in the aggregation processing unit 210 (step S876). For example, in a case where a user watches a video image held in a space 30 cm ahead as a video image, it is assumed that the aggregation processing unit 210 corrects the coordinate information of the pupil generated by the barycentric position generation unit 160.

As a result, in a case where it is determined that a blink of the left eye is detected (step S881: Yes), a left click process is performed (step S882). On the other hand, in a case where it is determined that a blink of the right eye is detected (step S883: Yes), a right click process is performed (step S884). Note that, in a case where it is determined that blinks of both eyes are detected (step S877: Yes), these processes are not performed.

In a case where any one of these blinks is detected and the pupil is completely hidden by blinking, control for redetection is executed (step S878). Then, screen drawing is performed on the display 320 (step S879). After that, the processing from step S873 is repeated.

Note that, in the application example described above, the pupil is detected and the area thereof is calculated; however, the area may be calculated by detecting an iris.

6. Fifth Application Example

Figure 10:
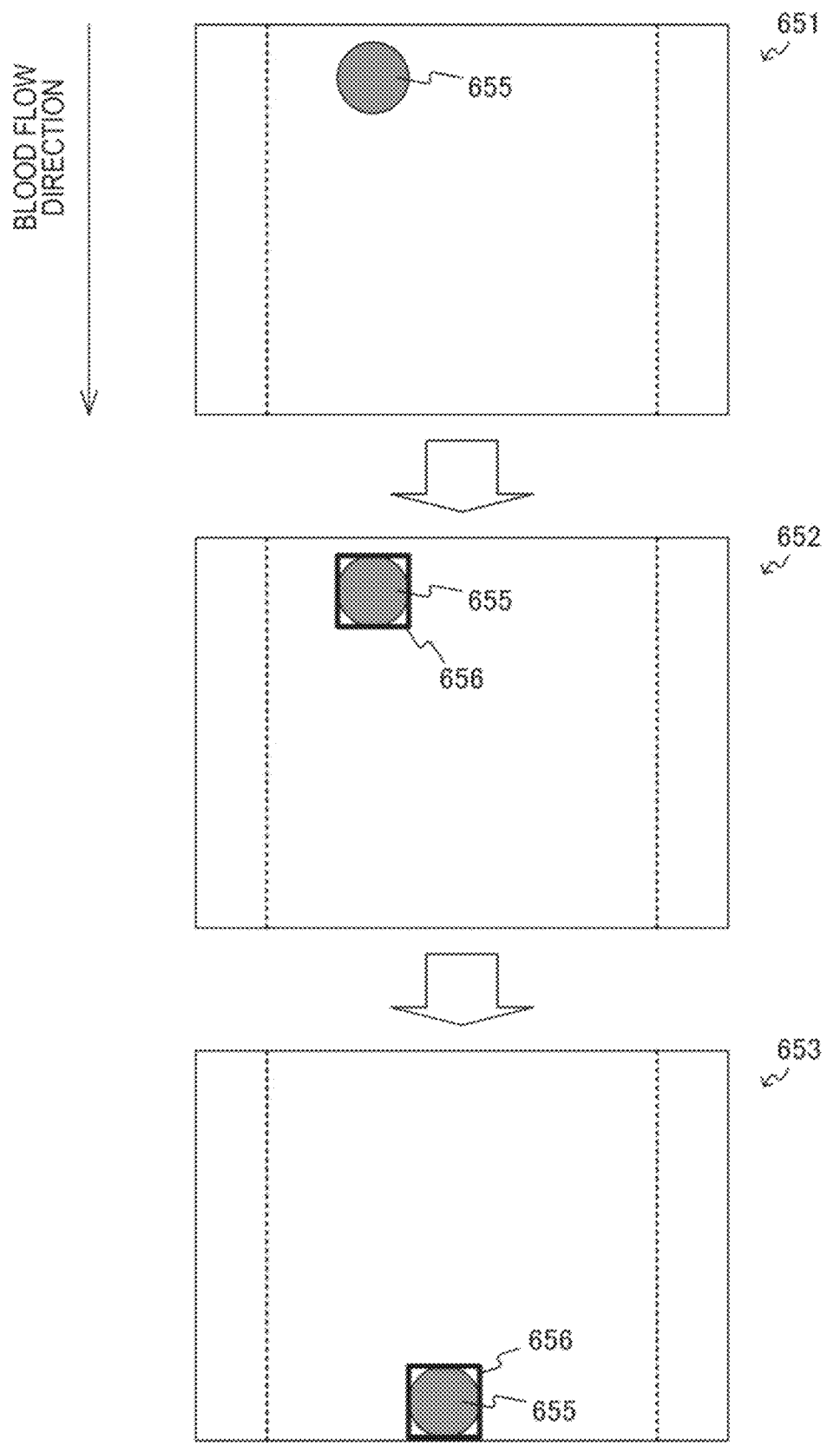
FIG. 10 is a diagram illustrating an example of blood flow velocity measurement in a fifth application example according to the embodiment of the present technology.

FIG. 10 is a diagram showing an example of blood flow velocity measurement in the fifth application example of the embodiment according to the present technology. Zebrafish is a small fish of the carp family, the most developed model vertebrate in the last decade. It is known that this zebrafish is suitable for studying the formation of the brain and internal organs because the inside of the body can be seen through. On the other hand, in order to capture the blood flow of this zebrafish, a speed of 600 fps is needed. In the image processing system according to the present embodiment, such observation is enabled by imaging the blood flow of the zebrafish at a high frame rate.

In order to measure the blood flow of zebrafish, a harmless color ball is firstly swallowed by zebrafish, as a target object of imaging. Then, as illustrated in an image 651, at the moment when the color ball 655 appears in the frame, recording is started together with the frame display 656 shown in an image 652. Then, as illustrated in an image 653, recording can be stopped when the color ball 655 has flown and the speed can be obtained from the number of frames.

Figure 11:
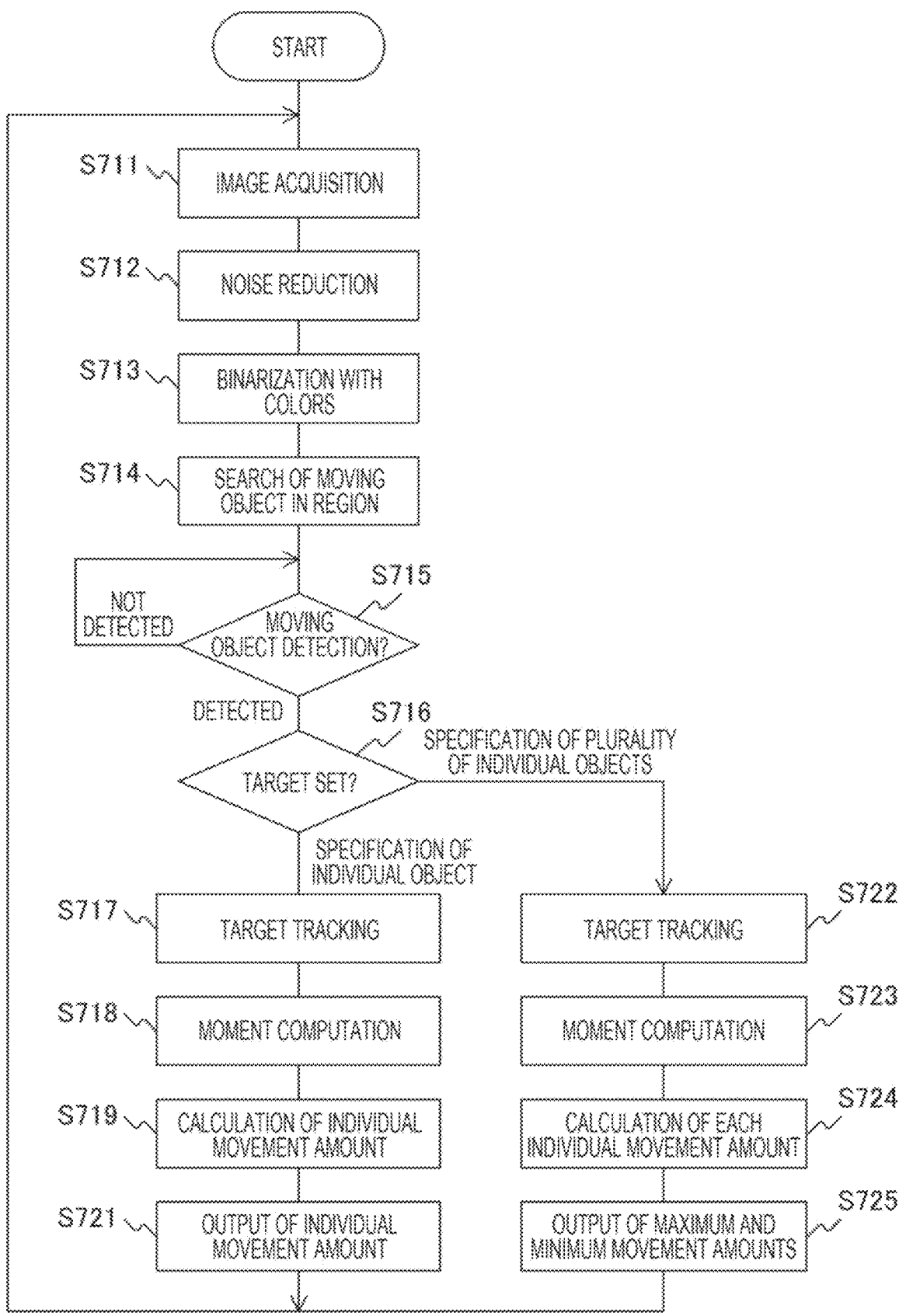
FIG. 11 is a flowchart illustrating an example of a processing procedure of the blood flow velocity measurement in the fifth application example according to the embodiment of the present technology.

FIG. 11 is a flowchart illustrating an example of a processing procedure of the blood flow velocity measurement in the fifth application example of the embodiment according to the present technology.

Firstly, image data to be measured is acquired (step S711). For this, for example, the image of the bloodstream area of the zebrafish can be captured by the imaging unit 110 through the microscope.

Noise which is not in the constant size is removed by the filter processing unit 120 in each acquired frame (step S712).

Furthermore, the binarization processing unit 130 performs binarization processing according to color components of the image data (step S713).

Then, a difference between frames adjacent in time series is generated by the tracking processing unit 140, and a moving object in the area specified by the operation input device 310 is searched (step S714). Here, it stands ready until the moving object is detected (step S715).

In a case where a single unit is specified as a tracking target by the operation input device 310 (step S716), the tracking processing unit 140 performs target tracking on the single unit (step S717). Then, for that single unit, the moment computation is performed by the moment generation unit 150 (step S718). Furthermore, with respect to the single unit, an individual movement amount is calculated by the barycentric position generation unit 160 (step S719). The individual movement amount obtained in this manner is displayed on the display 320 via the interface 230 (step S721).

On the other hand, in a case where a plurality of individuals are designated as tracking targets by the operation input device 310 (step S716), target tracking is performed on the plurality of individuals by the tracking processing unit 140 (step S722). Then, with respect to the plurality of individuals, moment computation is performed by the moment generation unit 150 (step S723). In addition, for the plurality of individuals, the respective individual movement amounts are calculated by the barycentric position generation unit 160 (step S724). The aggregation processing unit 210 sorts the obtained individual movement amounts and obtains a maximum value and a minimum value of the individual movement amounts. The maximum value and minimum value of these individual movement amounts are displayed on the display 320 via the interface 230 (step S725).

These processes are repeatedly performed on each of the frames of image data arranged in time series.

Note that, in this example, measurement of the blood flow velocity and calculation of the statistical value have been described; however, the blood flow velocity may be compared with an expected value stored in the database or the like and an abnormality may be detected in a case where a range of the expected value is not satisfied.

7. Sixth Application Example

Figure 12:
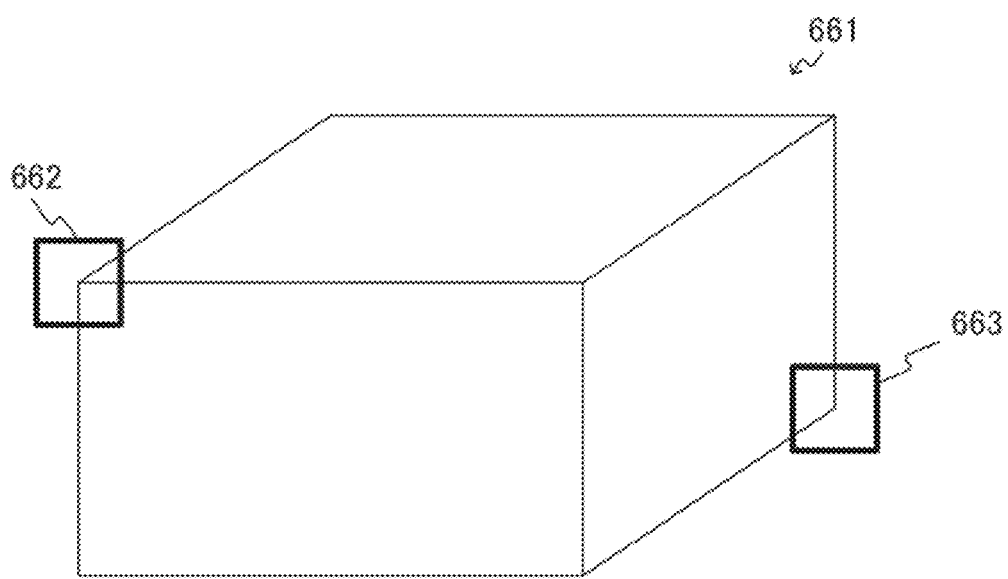
FIG. 12 is a diagram illustrating an example of malfunction detection by vibration amount measurement in a sixth application example according to the embodiment of the present technology.

FIG. 12 is a diagram illustrating an example of malfunction detection by vibration amount measurement in a sixth application example of the embodiment according to the present technology. In a vibration sensor which is usually used for measuring a vibration amount of a device, it is necessary to be directly connected to the device and safety has to be considered in addition to handling a trouble of fixing the sensor to the device. On the other hand, in a case of observing an appearance, for example, a frequency of a primary vibration of an engine at 1200 rpm (rotation per minute: revolutions per minute) during idling is about 20 Hz, but it becomes about 200 Hz at the time of operation. In the image processing system according to the present embodiment, the observation is made possible by capturing an image of the appearance of the device at a high frame rate.

In a case of observing the vibration amount of a device 661 which is a target object, the operation input device 310 designates the position and width as the observation target as illustrated by a frame 662 or 663 on the image. By observing the operation in the frames aligned in time series and comparing with the expected value for each area, malfunction of the device 661 can be detected.

Figure 13:
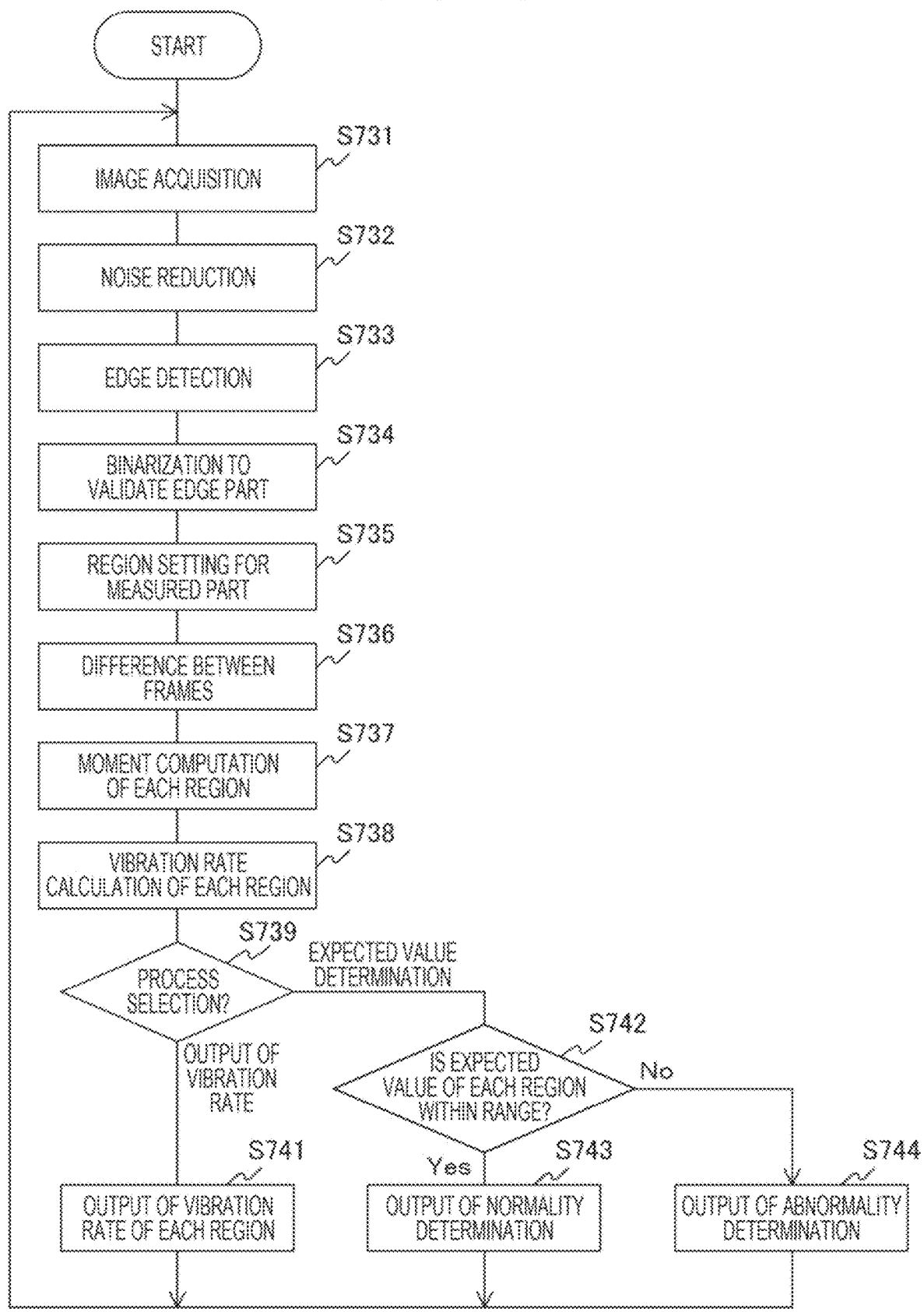
FIG. 13 is a flowchart illustrating an example of a processing procedure of the malfunction detection by the vibration amount measurement in the sixth application example according to the embodiment of the present technology.

FIG. 13 is a flowchart illustrating an example of a processing procedure of malfunction detection by vibration amount measurement in the sixth application example of the embodiment according to the present technology.

Firstly, image data to be measured is acquired (step S731). For the acquisition, for example, an image of the device to be measured is captured by the imaging unit 110.

In each acquired frame, noise is removed by the filter processing unit 120 (step S732). Furthermore, edge detection is performed by the filter processing unit 120 (step S733). Then, binarization processing for validating the detected edge part is performed by the binarization processing unit 130 (step S734).

In the frame of the image data to be measured, an area to be observed is set by the operation input device 310 (step S735). The set area is supplied from the control unit 220 to the tracking processing unit 140.

In the tracking processing unit 140, a difference between frames adjacent in time series is generated (step S736). Then, the moment computation is performed by the moment generation unit 150 for each set region (step S737). On the basis of the moment generated for each region, the aggregation processing unit 210 calculates a vibration rate for each region (step S738).

Thereafter, a process is selected according to an instruction from the operation input device 310 (step S739). In a case where the output of the vibration rate is given in instruction, the vibration rate of each region calculated by the aggregation processing unit 210 is displayed on the display 320 via the interface 230 (step S741).

In a case where the determination of the expected value of the vibration amount is given in instruction (step S739), the expected value stored in the database or the like is compared with the vibration rate of each region calculated by the aggregation processing unit 210. If the vibration rate is within the expected value range (step S742: Yes), the determination result indicating normality is displayed on the display 320 via the interface 230 (step S743). On the other hand, in a case where the vibration rate is significantly out of the expected value (step S742: No), a determination result indicating occurrence of abnormality is displayed on the display 320 via the interface 230 (step S744).

Note that these processes are repeatedly performed for each of the frames of the image data arranged in time series.

8. Seventh Application Example

Figure 14:
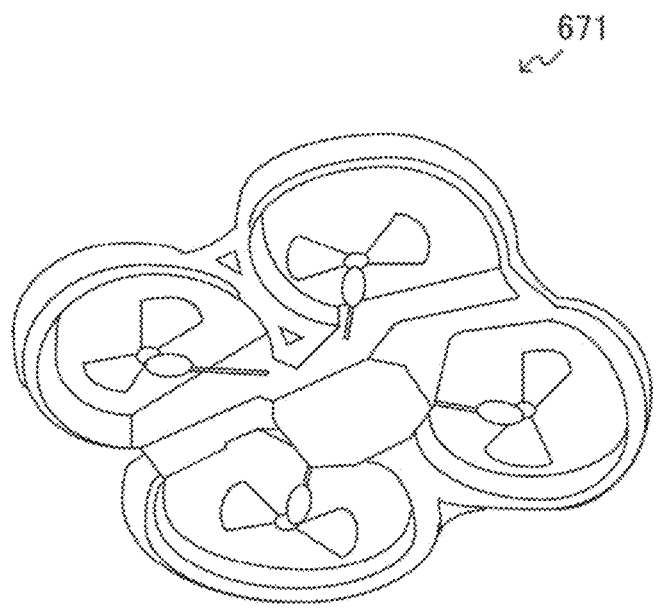
FIG. 14 is a diagram illustrating an example of malfunction detection by rotation amount measurement in a seventh application example according to the embodiment of the present technology.
Figure 14:
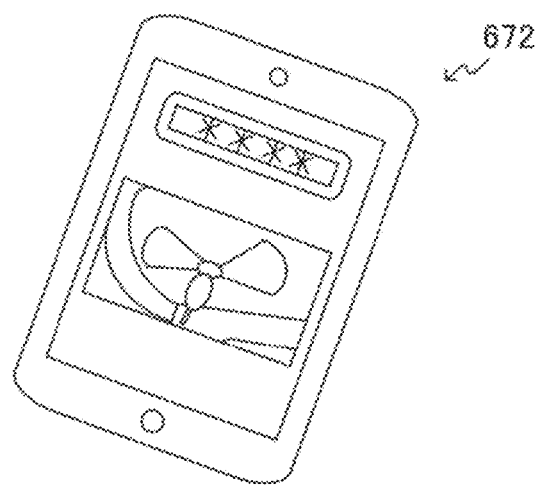

FIG. 14 is a diagram illustrating an example of malfunction detection by rotation amount measurement in a seventh application example of the embodiment according to the present technology. In a case where a propeller is provided in a main part of equipment such as a drone or a ventilator, malfunction can be detected by observing the rotation amount of the propeller as a target object. For example, the rotation amount is about 1500 to 1600 rpm in a case of a domestic fan, which is set "high", and about 2500 rpm in a case of a kitchen ventilation fan. Furthermore, a rotation amount is about 5000 to 6000 rpm in a case of a boat screw for full throttle, about 2300 to 2400 rpm in a case of a propeller of a propeller aircraft, and about 1300 to 2500 rpm in a case of a radio-controlled device or a drone.

Regarding the boat screw, the propeller of the propeller aircraft or the like, measurement can be performed with a built-in tachometer; however, detecting malfunction by objective observation from the outside is effective since there may be a failure of the tachometer. In the image processing system according to the present embodiment, the observation is made possible by capturing an image of the appearance of the device at a high frame rate.

For example, the camera of a mobile terminal 672 captures an image of a propeller portion of a drone 671 as a target object. In such a case, a sticker serving as a marker is put on a specific propeller of a plurality of propellers, and its movement amount can be measured by performing target tracking. Furthermore, it is also possible to perform edge detection and track the shape obtained by the edge detection.

By installing such an application in the mobile terminal 672, the rotation rate of the captured propeller portion can be displayed on the display unit of the mobile terminal 672 in real time.

Figure 15:
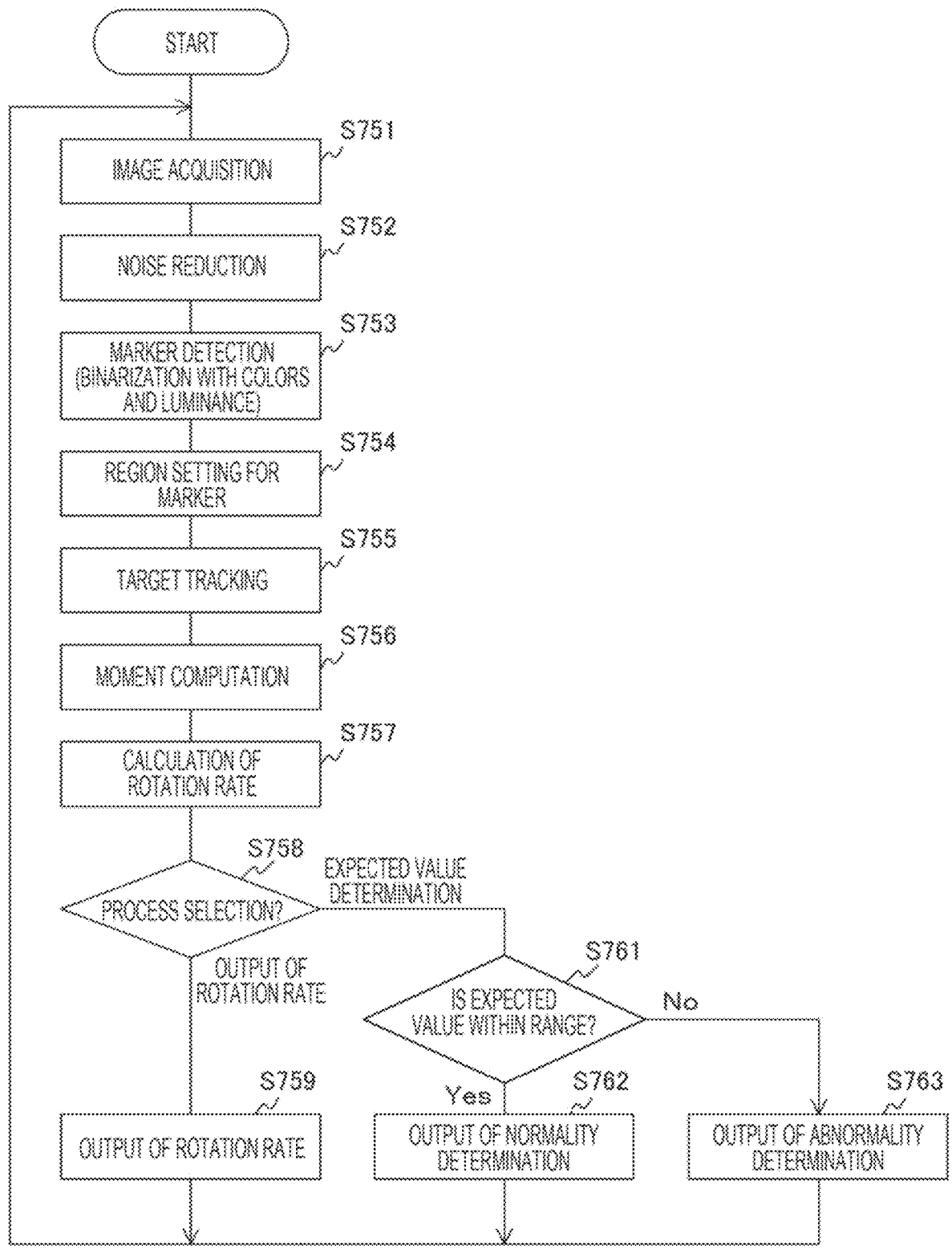
FIG. 15 is a flowchart illustrating an example of a processing procedure of the malfunction detection by the rotation amount measurement in the seventh application example according to the embodiment of the present technology.

FIG. 15 is a flowchart illustrating an example of a processing procedure of the malfunction detection by the rotation amount measurement in the seventh application example of the embodiment according to the present technology.

First, image data to be measured is acquired (step S751). For the acquisition, for example, an image of a propeller portion in a device to be measured is captured by the imaging unit 110.

In each acquired frame, noise is removed by the filter processing unit 120 (step S752). Then, binarization processing by color and luminance is performed by the binarization processing unit 130, and a marker of a sticker attached to the propeller portion is detected (step S753).

A region in the image is set according to the detected marker (step S754), and target tracking is performed by the tracking processing unit 140 (step S755). Furthermore, the moment computation is performed on the set region by the moment generation unit 150 (step S756). Then, on the basis of the generated moment, the rotation rate is calculated by the aggregation processing unit 210 (step S757).

Thereafter, a process is selected according to an instruction from the operation input device 310 (step S758). In a case where output of the rotation rate is given in instruction, the rotation rate calculated by the aggregation processing unit 210 is displayed on the display 320 via the interface 230 (step S759).

In a case where the determination of the expected value of the rotation rate is given in instruction (step S758), the expected value stored in database or the like is compared with the rotation rate calculated by the aggregation processing unit 210. In a case where the rotation rate is within the expected value range (step S761: Yes), the determination result indicating normality is displayed on the display 320 via the interface 230 (step S762). On the other hand, in a case where the rotation rate is significantly different from the expected value (step S761: No), a determination result indicating occurrence of an abnormality is displayed on the display 320 via the interface 230 (step S763).

Note that these processes are repeatedly performed for each of the frames of the image data arranged in time series.

As described above, according to the embodiment of the present technology, by capturing an image of a target object (a material body or a device) at a high frame rate and performing image processing in the image sensor, the measurement result can be quantified without outputting the image data. As a result, time for image analysis can be shortened and a data storage amount to be maintained can be reduced. In addition, since the calculation result can be generated at the sensor level, it can be realized even in a small system including a portable device.

It should be noted that the above-described embodiment represents an example for embodying the present technology, and matters in the embodiment and invention specifying matters in the claims have correspondence relationships, respectively. Likewise, the invention specifying matters in the claims and the matters in the embodiment of the present technology denoted by the same names have correspondence relationships. However, the present technology is not limited to the embodiment and can be embodied by subjecting the embodiment to various modifications without departing from the gist thereof.

Furthermore, the processing procedure described in the above embodiment may be regarded as a method having these series of procedures, as a program for causing a computer to execute these series of procedures, or as a recording medium for storing the program. As this recording medium, for example, a compact disc (CD), a mini disc (MD), a digital versatile disc (DVD), a memory card, a Blu-ray (registered trademark) disc (Blu-ray disc), or the like can be used.

Note that, the effects described in this specification are examples and should not be limited and there may be other effects.

Furthermore, the present technology may have following configurations.

(1) An image sensor including an imaging element configured to capture an image of an object and generate frames of image data arranged in time series, a binarization processing unit configured to binarize each of the frames to generate binarized frames, and a tracking processing unit configured to generate a difference between the binarized frames adjacent in time series and track a change in a position of the object included in the binarized frames.

(2) The image sensor according to (1), further including a filter processing unit configured to perform filter processing on each of the frames, in which the binarization processing unit performs the binarization process on each of the frames on which the filtering process has performed.

(3) The image sensor according to (1) or (2), further including a moment generation unit configured to calculate a moment of the binarized frames on the basis of a result of the tracking processing unit and generate a change amount of an area of the object included in the binarized frames.

(4) The image sensor according to (3), further including a barycentric position generation unit that generates a barycentric position of the object included in the binarized frame on the basis of the moment generated by the moment generation unit.

(5) The image sensor according to (4), further including an aggregation processing unit that performs aggregation processing on the object on the basis of a barycentric position of the object generated by the barycentric position generation unit.

(6) The image sensor according to (5), further including a display control unit for displaying the result of the aggregation processing by the aggregation processing unit.

(7) The image sensor according to (5), in which the aggregation processing unit tabulates at least one of the number, the size, and the movement rate of the object.

(8) The image sensor according (5), in which the aggregation processing unit detects a change in a shape of the object, and the tracking processing unit starts tracking in a case where the change of the shape of the object is detected.

(9) The image sensor according to (5), in which the aggregation processing unit measures a speed of the object and calculates a statistical value of the speed of the object in a case where there are a plurality of the objects.

(10) The image sensor according to (5), in which
the imaging element captures an image of an eye of a living body as the object,
the binarization processing unit detects a pupil in the captured image of the eye of the living body,
the tracking processing unit tracks line-of-sight in the captured image of the eye of the living body,
the moment generation unit calculates an area of the pupil in the captured image of the eye of the living body, and
the aggregation processing unit detects blinking on the basis of the area of the pupil and time during which the pupil is continuously recognized.

(11) The image sensor according to (10), further including an interface configured to accept an operation input according to a manner of the blinking.

(12) The image sensor according to (10), in which
the barycentric position generation unit generates a barycentric position of the pupil in the captured image of the eye of the living body, and
the aggregation processing unit determines a line-of-sight direction on the basis of the barycentric position of the pupil.

(13) The image sensor according to (12), further including an interface configured to accept an operation input according to a manner of the blinking and the line-of-sight direction.

(14) The image sensor according to (10), in which the aggregation processing unit controls the binarization processing unit to perform detection of the pupil again when the blinking is detected.

(15) The image sensor according to (5), in which the aggregation processing unit measures a speed of the object and detects an abnormality in a case where the speed of the object does not satisfy a predetermined condition.

(16) The image sensor according to (5), in which the aggregation processing unit measures a vibration amount of the object and detects an abnormality in a case where the vibration amount of the object does not satisfy a predetermined condition.

(17) The image sensor according to (5), in which the aggregation processing unit measures a rotation amount of the object and detects an abnormality in a case where the rotation amount of the object does not satisfy a predetermined condition.

REFERENCE SIGNS LIST

100 Image sensor
110 Imaging unit
120 Filter processing unit
130 Binarization processing unit
140 Tracking processing unit
150 Moment generation unit
160 Barycentric position generation unit
200 Aggregation unit
210 Aggregation processing unit
220 Control unit
230 Interface
310 Operation input device
320 Display

The invention claimed is:
1. An image sensor, comprising:
an imaging element configured to:
capture an image of an object and;
generate frames of image data in time series based on the captured image;
a binarization processing unit configured to binarize each of the frames to generate binarized frames;
a tracking processing unit configured to:
generate a difference between the binarized frames adjacent in time series; and
track a change in a position of the object included in the binarized frames based on the difference, wherein
the imaging element captures an image of an eye of a living body as the object,
the binarization processing unit is further configured to detect a pupil in the captured image of the eye of the living body, and
the tracking processing unit is further configured to track line-of-sight in the captured image of the eye of the living body;
a moment generation unit configured to calculate an area of the pupil in the captured image of the eye of the living body; and
an aggregation processing unit configured to detect blinking based on the area of the pupil and a time during which the pupil is continuously recognized.

2. The image sensor according to claim 1, further comprising
a filter processing unit configured to filter each of the frames, wherein the binarization processing unit is configured to binarize each of the filtered frames.

3. The image sensor according to claim 1, wherein the moment generation unit is further configured to calculate a moment of the object included in the binarized frames based on a result of the tracking processing unit.

4. The image sensor according to claim 3, further comprising a barycentric position generation unit configured to generate a barycentric position of the object included in the binarized frames based on the moment calculated by the moment generation unit.

5. The image sensor according to claim 4, wherein the aggregation processing unit configured to execute an aggregation process related to the object based on the barycentric position of the object generated by the barycentric position generation unit.

6. The image sensor according to claim 5, further comprising a display control unit configured to display a result of the aggregation process.

7. The image sensor according to claim 5, wherein the aggregation processing unit is further configured to aggregate at least one of a number of the object, a size of the object, a movement rate of the object.

8. The image sensor according to claim 5, wherein
the aggregation processing unit is further configured to detect a change in a shape of the object, and
the tracking processing unit is configured to track the object in a case where the change of the shape of the object is detected.

9. The image sensor according to claim 5, wherein the aggregation processing unit is further configured to:
measure a speed of the object; and
calculate a statistical value of the speed of the object based on presence of a plurality of objects including the object.

10. The image sensor according to claim 1, further comprising an interface configured to accept an operation input based on a manner of the blinking.

11. The image sensor according to claim 1,
further comprising a barycentric position generation unit configured to generate a barycentric position of the pupil in the captured image of the eye of the living body, wherein
the aggregation processing unit is further configured to determine a line-of-sight direction based on the barycentric position of the pupil.

12. The image sensor according to claim 11, further comprising an interface configured to accept an operation input based on a manner of the blinking and the line-of-sight direction.

13. The image sensor according to claim 1, wherein the aggregation processing unit is further configured to control the binarization processing unit to detect the pupil again in a case where the blinking is detected.

14. The image sensor according to claim 5, wherein the aggregation processing unit further configured to:
measure a speed of the object; and
detect an abnormality in a case where the speed of the object does not satisfy a determined condition.

15. The image sensor according to claim 5, wherein the aggregation processing unit is further configured to:
measure a vibration amount of the object; and
detect an abnormality in a case where the vibration amount of the object does not satisfy a determined condition.

16. The image sensor according to claim 5, wherein the aggregation processing unit is further configured to:
measure a rotation amount of the object; and
detect an abnormality in a case where the rotation amount of the object does not satisfy a determined condition.

17. An image sensor, comprising:
an imaging element configured to:
capture an image of an object; and
generate frames of image data in time series based on the captured image;
a binarization processing unit configured to binarize each of the frames to generate binarized frames;
a tracking processing unit configured to:
generate a difference between the binarized frames adjacent in time series; and
track a change in a position of the object included in the binarized frames based on the difference;
a moment generation unit configured to calculate a moment of the object included in the binarized frames based on a result of the tracking processing unit;
a barycentric position generation unit configured to generate a barycentric position of the object included in the binarized frames based on the moment generated by the moment generation unit; and
an aggregation processing unit configured to execute aggregation processing related to the object based on the barycentric position of the object generated by the barycentric position generation unit, wherein
the imaging element captures an image of an eye of a living body as the object,
the binarization processing unit is further configured to detect a pupil in the captured image of the eye of the living body,
the tracking processing unit is further configured to track line-of-sight in the captured image of the eye of the living body,
the moment generation unit is further configured to calculate an area of the pupil in the captured image of the eye of the living body, and
the aggregation processing unit is further configured to detect blinking based on the area of the pupil and time during which the pupil is continuously recognized.

* * * * *